United States Patent
Hattori et al.

(10) Patent No.: US 6,297,267 B1
(45) Date of Patent: Oct. 2, 2001

(54) 4,5-DIARYLOXAZOLE COMPOUNDS

(75) Inventors: Kouji Hattori, Takarazuka; Naoaki Fujii, Takatsuki; Akira Tanaka, Takarazuka; Fujiko Takamura, Izumi, all of (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/529,405
(22) PCT Filed: Oct. 1, 1998
(86) PCT No.: PCT/JP98/04455
  § 371 Date: Apr. 26, 2000
  § 102(e) Date: Apr. 26, 2000
(87) PCT Pub. No.: WO99/21843
  PCT Pub. Date: May 6, 1999

(30) Foreign Application Priority Data

Oct. 27, 1997 (AU) .................................................. PP0032

(51) Int. Cl.$^7$ ......................... A61K 31/42; C07D 263/30
(52) U.S. Cl. ............................................. 514/374; 548/235
(58) Field of Search ............................... 548/235; 514/374

(56) References Cited

U.S. PATENT DOCUMENTS

| | | |
|---|---|---|
| 5,763,489 | 6/1998 | Taniguchi et al. . |
| 5,863,918 | 1/1999 | Taniguchi et al. . |
| 5,972,965 | 10/1999 | Taniguchi et al. . |
| 6,025,375 | * 2/2000 | Taniguchi et al. . |

* cited by examiner

Primary Examiner—Floyd D. Higel
Assistant Examiner—Ebenezer Sackey
(74) Attorney, Agent, or Firm—Oblon, Spivak, McClelland, Maier & Neustadt, P.C.

(57) ABSTRACT

A compound of the formula:

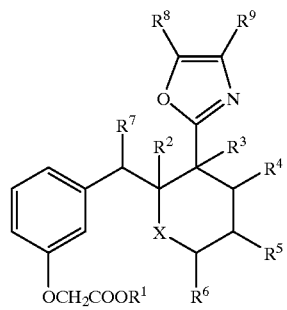

wherein $R^1$ is a hydrogen atom or a carboxy protective group, $R^2$, $R^5$, $R^6$ and $R^7$ are each a hydrogen atom or a hydroxy group, $R^3$ and $R^4$ are each a hydrogen atom, or are combined together to form an epoxy group or a single bond. $R^8$ and $R^9$ are each an optionally substituted aryl group, and X is a single bond or a methylene group, in addition to the above definitions. $R^2$ and $R^3$ may be combined together to form a single bond; provided that when $R^2$, $R^5$, $R^6$ and $R^7$ are each a hydrogen atom, then $R^3$ and $R^4$ are combined together to form an epoxy group; when $R^3$ and $R^4$ are combined together to form a single bond, then at least one of $R^2$, $R^5$, $R^6$ and $R^7$ is a hydroxy group and the others are hydrogen; and when $R^3$ and $R^4$ are each a hydrogen atom, then at least one of $R^2$, $R^5$, $R^6$ and $R^7$ is a hydroxy group and the others are hydrogen, and X is a methylene group, or its salt.

13 Claims, No Drawings

4,5-DIARYLOXAZOLE COMPOUNDS

This application is a 371 of PCT/JP98/04455 filed Oct. 1, 1998.

1. Technical Field

This invention relates to new 4,5-diaryloxazole compounds and pharmaceutically acceptable salts thereof which are useful as a medicament.

2. Background Art

Prostaglandins are known as autacoids that show a various kind of biological effects. Specifically, prostaglandin $I_2$ (hereinafter, referred as $PGI_2$) is known to have inhibitory activity on platelet aggregation, vasodilating activity, antihypertensive activity and the like. Therefore, $PGI_2$ agonists are expected to show the above activities which are useful as a medicament for therapeutic and/or prophylactic treatment of arterial obstruction, cerebrovascular disease, hepatic cirrhosis, arteriosclerosis, ischemic heart disease, restenosis after percutaneous transluminal coronary angioplasty, hypertension, dermatosis or the like.

So far, some 4,5-diaryloxazole compounds having pharmacological activities as $PGI_2$ agonists have been known, for example, in WO 95/17393, WO 95/24393, WO 97/03973, EP 0 542 203 and U.S. Pat. No. 5,362,879.

DISCLOSURE OF INVENTION

This invention relates to 4,5-diaryloxazole compounds having novel structures. More particularly, it relates to new 4,5-diaryloxazole compounds and pharmaceutically acceptable salts thereof, their production process, a pharmaceutical composition containing the same and a use thereof for the manufacture of medicaments.

Accordingly, an object of this invention is to provide new and useful 4,5-diaryloxazole compounds and pharmaceutically acceptable salts thereof.

Another object of this invention is to provide processes for the production of the 4,5-diaryloxazole compounds and salts thereof.

A further object of this invention is to provide a pharmaceutical composition containing, as an active ingredient, said 4,5-diaryloxazole compounds or pharmaceutically acceptable salts thereof.

Another object of this invention is to provide a use of the 4,5-diaryloxazole compounds and pharmaceutically acceptable salts thereof as a prostaglandin $I_2$ agonist.

Still further object of this invention is to provide a use of the 4,5-diaryloxazole compounds and pharmaceutically acceptable salts thereof for the manufacture of medicament for therapeutic and/or prophylactic treatment of arterial obstruction, cerebrovascular disease, hepatic cirrhosis, arteriosclerosis, ischemic heart disease, restenosis after percutaneous transluminal coronary angioplasty, hypertension, dermatosis or the like.

The 4,5-diaryloxazole compounds of this invention can be represented by the following formula (I):

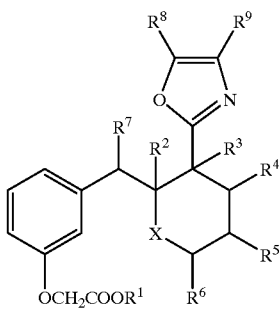

(I)

wherein $R^1$ is a hydrogen atom or a carboxy protective group, $R^2$, $R^5$, $R^6$ and $R^7$ are each a hydrogen atom or a hydroxy group, $R^3$ and $R^4$ are each a hydrogen atom, or are combined together to form an epoxy group or a single bond, $R^8$ and $R^9$ are each an optionally substituted aryl group, and X is a single bond or a methylene group, in addition to the above definitions, $R^2$ and $R^3$ may be combined together to form a single bond;

provided that when $R^2$, $R^5$, $R^6$ and $R^7$ are each a hydrogen atom, then $R^3$ and $R^4$ are combined together to form an epoxy group;

when $R^3$ and $R^4$ are combined together to form a single bond, then at least one of $R^2$, $R^5$, $R^6$ and $R^7$ is a hydroxy group and the other(s) is(are) hydrogen atom(s); and when $R^3$ and $R^4$ are each a hydrogen atom, then at least one of $R^2$, $R^5$, $R^6$ and $R^7$ is a hydroxy group and the other(s) is(are) hydrogen atom(s), and X is a methylene group.

The new 4,5-diaryloxazole compounds (I) can be prepared by the following processes.

Process 1

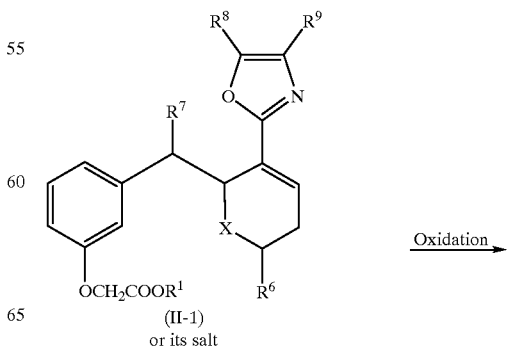

(II-1)
or its salt

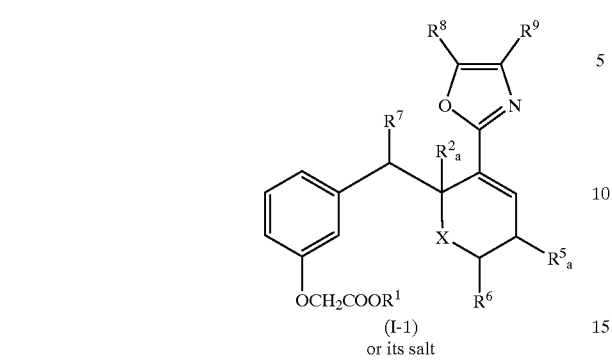
(I-1)
or its salt
Process 2
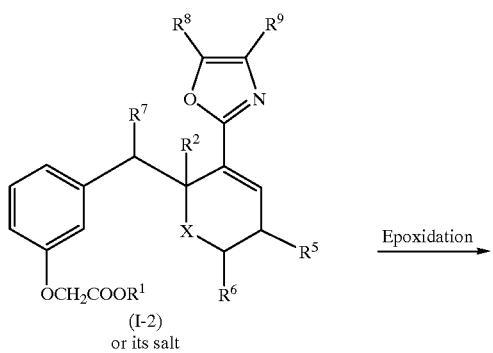
(I-2)
or its salt
Epoxidation →
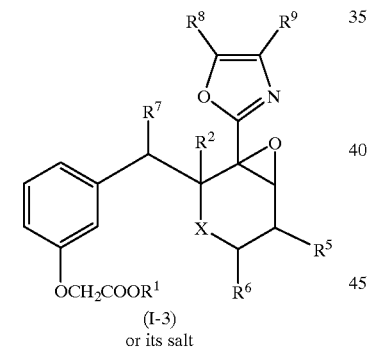
(I-3)
or its salt
Process 3
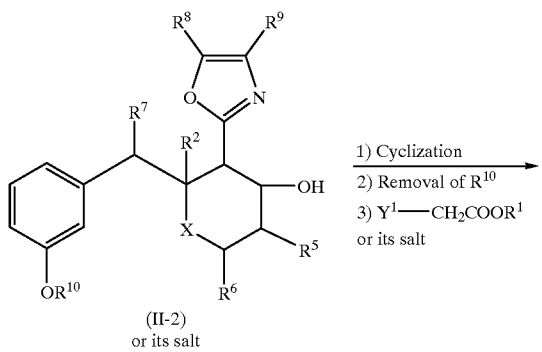
(II-2)
or its salt
1) Cyclization
2) Removal of $R^{10}$
3) $Y^1$—$CH_2COOR^1$
or its salt
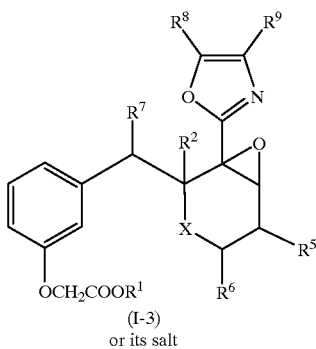
(I-3)
or its salt
Process 4
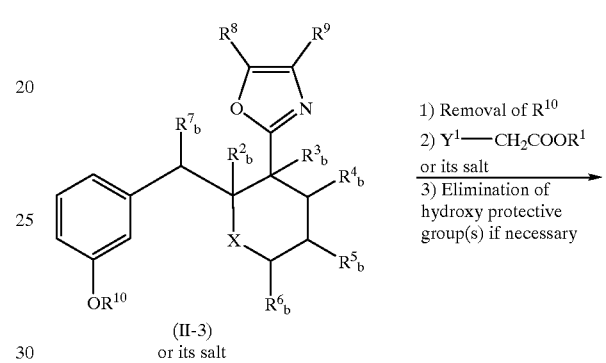
(II-3)
or its salt
1) Removal of $R^{10}$
2) $Y^1$—$CH_2COOR^1$
or its salt
3) Elimination of hydroxy protective group(s) if necessary →
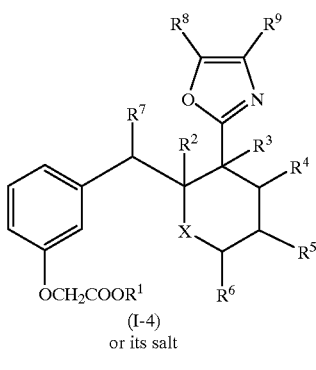
(I-4)
or its salt
Process 5
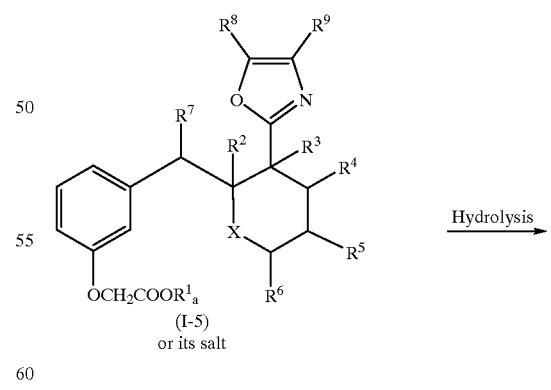
(I-5)
or its salt
Hydrolysis →

-continued

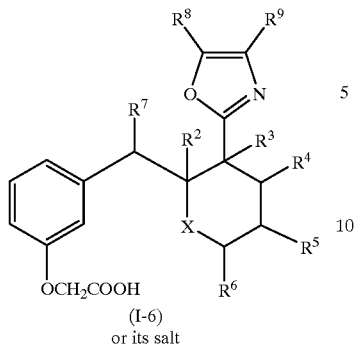

(I-6)
or its salt wherein $R^1$, $R^2$, $R^3$, $R^4$, $R^5$, $R^6$, $R^7$, $R^8$, $R^9$ and X are as defined above, $Y^1$ is a leaving group, $R^{10}$ is a hydroxy protective group, $R^1{}_a$ is a carboxy protective group, any one of $R^2{}_a$ and $R^5{}_a$ is a hydroxy group and the other is a hydrogen atom or a hydroxy group, $R^2{}_b$, $R^5{}_b$, $R^6{}_b$ and $R^7{}_b$ are each a hydrogen atom, a hydroxy group or a protected hydroxy group, and $R^3{}_b$ and $R^4{}_b$ are each a hydrogen atom or are combined together to form a single bond, in addition to the above definitions, $R^2{}_b$ and $R^3{}_b$ may be combined together to form a single bond.

Some of the starting compounds are novel and can be prepared by the following processes.

Process A

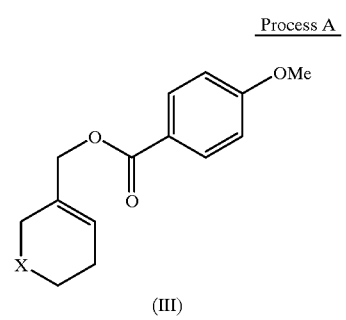

(III)

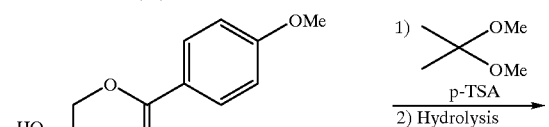

(IV)

(V)

-continued

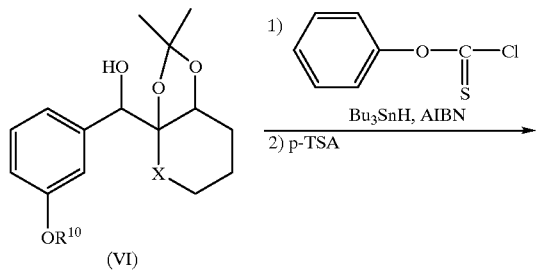

(VI)

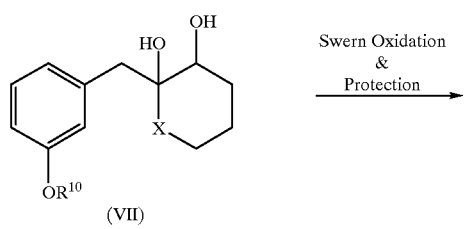

(VII)

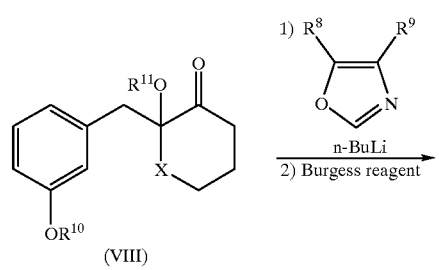

(VIII)

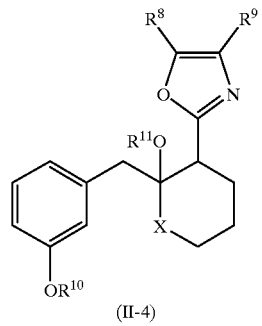

(II-4)

Process B

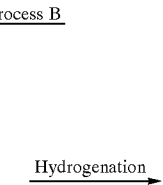

(II-4)

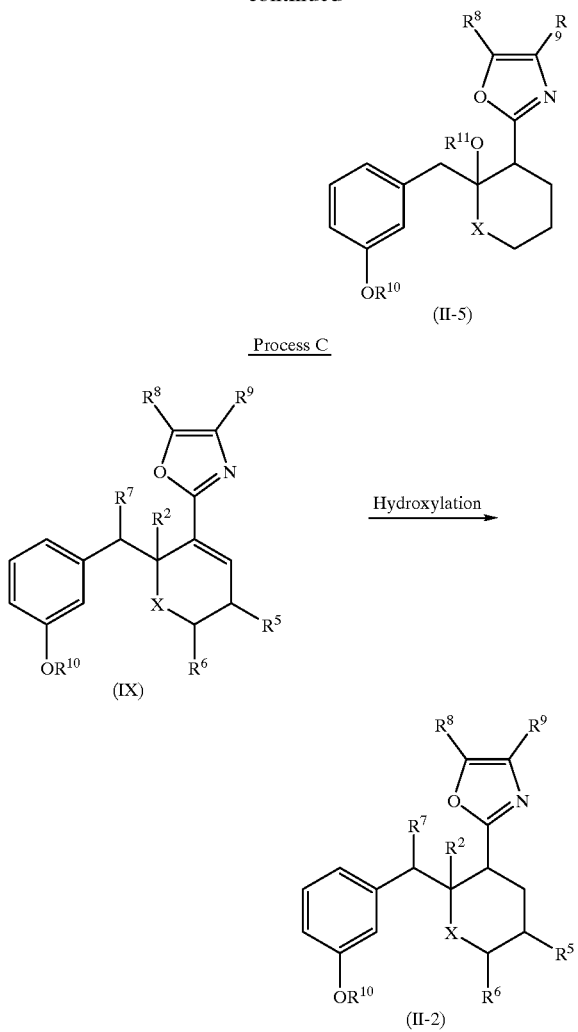

Process C

Hydroxylation wherein $R^2$, $R^5$, $R^6$, $R^7$, $R^8$, $R^9$, $R^{10}$ and X are as defined above, and $R^{11}$ is a hydroxy protective group; AIBN means 2,2'-azobis(isobutyronitrile) and p-TSA means p-toluenesulphonic acid.

Suitable pharmaceutically acceptable salts of the object compounds (I) are conventional non-toxic salts, specifically metal salts such as alkali metal salts (e.g., sodium or potassium salt) and alkaline earth metal salts (e.g., calcium or magnesium salt), ammonium salts, organic base salts (e.g., trimethylamine, triethylamine, pyridine, picoline, dicyclohexylamine or dibenzylethylenediamine salt), organic acid salts (e.g., acetate, maleate, tartrate, methanesulfonate, benzenesulfonate, formate, toluenesulfonate or trifluoroacetate), inorganic acid salts (e.g., hydrochloride, hydrobromide, sulfate or phosphate), salts with an amino acid (e.g., arginine salt, aspartate or glutamate) and the like.

In the above and subsequent descriptions of the present specification, suitable examples and illustrations of the various definitions which the present invention includes within the scope thereof are explained in detail as follows.

The term "lower" is intended to mean 1 to 6 carbon atoms, unless otherwise indicated.

Suitable lower alkyl groups may include straight or branched ones having 1 to 6 carbon atoms, such as methyl, ethyl, propyl, isopropyl, butyl, isobutyl, sec-butyl, t-butyl, pentyl, isopentyl, hexyl or the like, preferably the one having 1 to 4 carbon atoms.

Suitable aryl groups may contain 6 to 12 carbon atoms and may be optionally substituted with suitable substituent (s) such as a halogen, amino, hydroxy, a lower alkyl, a lower alkoxy or the like. Specific examples thereof are phenyl, tolyl, xylyl, mesityl, cumenyl and naphthyl.

Suitable carboxy protective groups may include lower alkyl groups (e.g., methyl, ethyl or tert-butyl), mono-(or di- or tri-)halo(lower)alkyl groups (e.g., 2-iodomethyl or 2,2,2-trichloroethyl), ar(lower)alkyl groups (e.g., benzyl) and the like, among which the lower alkyl group is preferred.

Suitable hydroxy protective groups may include lower alkyl, benzyl, acyl, tri(lower)alkylsilyl, diaryl(lower) alkylsilyl and the like.

Suitable examples of the lower alkyl groups are those as exemplified above.

Suitable examples of the acyl groups may include aliphatic acyl groups such as a lower alkanoyl (e.g., formyl, acetyl, propionyl, butyryl, isobutyryl, valeryl, isovaleryl, oxalyl, succinyl or pivaloyl), a lower alkoxycarbonyl (e.g., methoxycarbonyl or ethoxycarbonyl), a lower alkanesulfonyl (e.g., mesyl or ethanesulfonyl), and an arenesulfonyl (e.g. benzenesulfonyl or tosyl); and acyl groups containing an aromatic or heterocyclic ring such as an aroyl (e.g., benzoyl, toluoyl, xyloyl, naphthoyl, phthaloyl or indancarbonyl), an ar(lower)alkanoyl (e.g., phenylacetyl or phenylpropionyl), an ar(lower)alkoxycarbonyl (e.g., benzyloxycarbonyl or phenethyloxycarbonyl), and the like.

Suitable examples of the tri(lower)alkylsilyl groups may include trimethylsilyl, triethylsilyl, triisopropylsilyl, dimethylisopropylsilyl, tert-butyldimethylsilyl and the like.

Suitable examples of the diaryl(lower)alkylsilyl groups may include tert-butyldiphenylsilyl and the like.

Suitable leaving groups may include a halogen (e.g., chlorine, bromine, iodine or fluorine), a lower alkoxy (e.g., methoxy, ethoxy, propoxy, isopropoxy or butoxy) and the like.

Preferred embodiments of the object compounds (I) are as follows:

Compounds of the formula (I), wherein $R^1$ is a hydrogen atom or a carboxy protective group, any one of $R^2$, $R^5$, $R^6$ and $R^7$ is a hydroxy group and the others are hydrogen atoms, $R^3$ and $R^4$ are each a hydrogen atom, $R^8$ and $R^9$ are each a phenyl group, and X is a methylene group; compounds of the formula (I), wherein $R^1$ is a hydrogen atom or a carboxy protective group, any one of $R^2$, $R^5$, $R^6$ and $R^7$ is a hydroxy group and the others are hydrogen atoms, $R^3$ and $R^4$ are combined together to form an epoxy group or a single bond, $R^8$ and $R^9$ are each a phenyl group, and X is a single bond or a methylene group; and X is a single bond or a methylene group; and compounds of the formula (I), wherein $R^1$ is a hydrogen atom or a carboxy protective group, $R^2$, $R^5$, $R^6$ and $R^7$ are each a hydrogen atom, $R^3$ and $R^4$ are combined together to form an epoxy group, $R^8$ and $R^9$ are each a phenyl group, and X is a single bond or a methylene group.

More specifically, the preferred embodiments are as follows:

(1) sodium {3-{[2-(4,5-diphenyloxazol-2-yl)-1-hydroxy-2-cyclohexen-1-yl]methyl}phenoxy}acetate,
(2) sodium {3-{[(1S)-2-(4,5-diphenyloxazol-2-yl)-4-hydroxy-2-cyclohexen-1-yl]methyl}phenoxy}acetate,
(3) sodium {3-{[(1S)-2-(4,5-diphenyloxazol-2-yl)-2,3-epoxy-1-cyclohexyl]methyl}phenoxy}acetate,
(4) sodium (R)-{3-{[2-(4,5-diphenyloxazol-2-yl)-1-hydroxy-2-cyclohexen-1-yl]methyl}-phenoxy}acetate,
(5) sodium {3-{[(1R,2S)-2-(4,5-diphenyloxazol-2-yl)-1-hydroxy-1-cyclohexyl]methyl}phenoxy}acetate,
(6) sodium (S)-{3-{[2-(4,5-diphenyloxazol-2-yl)-1-hydroxy-2-cyclohexen-1-yl]methyl}phenoxy}acetate,
(7) sodium (S)-{3-{[2-(4,5-diphenyloxazol-2-yl)-1-hydroxy-2-cyclopenten-1-yl]methyl}phenoxy}acetate,
(8) sodium (R)-{3-{[2-(4,5-diphenyloxazol-2-yl)-1-hydroxy-2-cyclopenten-1-yl]methyl}phenoxy}acetate,
(9) sodium {3-{[(1S,2R,3S)-2-(4,5-diphenyloxazol-2-yl)-2,3-epoxy-1-cyclohexyl]methyl}phenoxy}acetate,
(10) sodium {3-{[(1S,2S,3R)-2-(4,5-diphenyloxazol-2-yl)-2,3-epoxy-1-cyclohexyl]methyl}phenoxy}acetate, and
(11) sodium {3-{[(1S)-2-(4,5-diphenyloxazol-2-yl)-2,3-epoxy-1-cyclopentyl]methyl}phenoxy}acetate.

It is to be noted that the object compounds (I) may include one or more stereoisomers due to asymmetric carbon atom (s) and double bond, and that all of such isomers and a mixture thereof are included within the scope of the present invention.

It is further to be noted that isomerization or rearrangement of the object compounds (I) may occur due to the effect of the light, acid, base or the like, and the compounds obtained as the result of said isomerization or rearrangement is also included within the scope of the present invention.

It is also to be noted that the solvating form of the compounds (I) (e.g., hydrate) and any crystalline form of the compounds (I) are included within the scope of the present invention.

Also included in the scope of the invention are radiolabelled derivatives of the compounds (I) which are suitable for biological studies.

The processes for preparing the object and starting compounds of the present invention are explained in detail in the following.

Process 1

A compound (I-1) or its salt can be prepared by treating a compound (II-1) or its salt with an oxidant which is capable of oxidizing at the allylic position in the compound (II-1).

Suitable oxidants are selenium dioxide, or the like.

The reaction is usually carried out in a conventional solvent such as water, an alcohol (e.g., methanol, ethanol or isopropyl alcohol), tetrahydrofuran, dioxane, dichloromethane, ethylene dichloride, chloroform, N,N-dimethylformamide, N,N-dimethylacetamide or any other organic solvent which does not adversely affect the reaction.

The reaction may be usually carried out under cooling to heating since the reaction temperature is not critical.

The compound (I-1) can be also prepared by (1) reacting the corresponding allylic hydroperoxide, which is prepared by reacting a compound (II-1) with singlet oxygen, an alkali (e.g., sodium hydroxide) or a reducing agent (e.g., sulfide) or (2) hydrolysis of the corresponding allylic ester, which is prepared by reacting a compound (II-1) with a lower alkyl peroxycarboxylate (e.g., tert-butyl peroxyacetate, hydroperoxide or tert-butyl perbenzoate).

Process 2

A compound (I-3) or its salt can be prepared by subjecting a compound (I-2) or its salt to an epoxidation.

Epoxidation of a double bond in the cyclopentene or cyclohexene ring can be accomplished by using an oxidant, for example, hydrogen peroxide or its derivatives. Suitable derivatives of the hydrogen peroxides are a lower alkyl hydroperoxide (e.g., tert-butyl hydroperoxide), a peroxy acid (e.g., peroxyacetic acid, peroxytrifluoroacetic acid or m-chloroperoxybenzoic acid) or the like. Other oxidants such as dimethyldioxirane, ozone, sodium hypochlorite or the like may be used for the epoxidation.

This reaction is preferably carried out in the presence of an inorganic base or an organic base such as an alkali metal [e.g., sodium or potassium], hydroxide, carbonate or bicarbonate thereof, a trialkylamine [e.g., trimethylamine or triethylamine] or the like.

The reaction is usually carried out in a conventional solvent such as water, an alcohol (e.g., methanol, ethanol or isopropyl alcohol), tetrahydrofuran, dioxane, dichloromethane, ethylene dichloride, chloroform, N,N-dimethylformamide, N,N-dimethylacetamide or any other organic solvent which does not adversely affect the reaction.

The reaction may be usually carried out under cooling to heating since the reaction temperature is not critical.

Process 3

A compound (I-3) or its salt can be also prepared by subjecting a compound (II-2) or its salt to 1) a cyclization reaction, 2) a removal of a hydroxy protective aroup in the phenol residue and then 3) a reaction with $Y^1$—$CH_2COOR^1$ or its salt.

The cyclization can be accomplished by reacting a dihydroxy compound (II-2) or its salt with orthoactic acid trimethyl ester and p-toluenesulfonic acid.

The reaction is usually carried out in a conventional solvent such as tetrahydrofuran, 1,4-dioxane, 1,2-dimethoxyethane, methylene chloride, chloroform, dimethylformamide or any other organic solvent which does not adversely affect the reaction.

The reaction may be usually carried out under cooling to heating since the reaction temperature is not critical.

The removal of the hydroxy protective group in the phenol residue can be carried out by a conventional method known in the art to give a phenol residue, e.g., by treating with tetrabutylammonium fluoride.

The reaction of the resultant phenol compound with a compound of the formula $Y^1$—$CH_2COOR^1$ is preferably carried out in the presence of a base in the case where $Y^1$ is a halogen atom.

Suitable $Y^1$—$CH_2COOR^1$ may include halo-acetates such as methyl or ethyl bromoacetate, methyl or ethyl chloroacetate and methyl or ethyl iodoacetate.

Suitable bases may include inorganic bases and organic bases such as an alkali metal [e.g., sodium or potassium], hydroxide, carbonate or bicarbonate thereof, a trialkylamine [e.g., trimethylamine or triethylamine] or the like.

The reaction is usually carried out in a solvent such as water, an alcohol [e.g., methanol or ethanol], methylene chloride, tetrahydrofuran, 1,2-dimethoxyethane, a mixture thereof or any other solvent which does not adversely influence the reaction. A liquid base can be also used as a solvent.

The reaction may be usually carried out under cooling to warming since the reaction temperature is not critical.

Process 4

A compound (I-4) or its salt can be prepared by subjecting a compound (II-3) or its salt to 1) a removal of a hydroxy protective group in the phenol residue, 2) a reaction with a compound of the formula $Y^1$—$CH_2COOR^1$ and then 3) a removal of protective group(s) from the remaining protected hydroxy group(s) for $R^2_b$, $R^5_b$, $R^6_b$ and $R^7_b$, if necessary.

The reaction of the above steps 1) and 2) can be carried out in the same manner as the steps 2) and 3) in the above Process 3, respectively.

And the removal of the hydroxy protective group(s) in the step 3) can be carried out by a conventional method, e.g., using tetrabutylammonium fluoride.

Process 5

A compound (I-6) or its salt can be prepared by subjecting a compound (I-5) or its salt to an elimination of the carboxy protective group for $R^1_a$.

This reaction can be conducted by a conventional method such as hydrolysis or the like.

The hydrolysis is preferably carried out in the presence of a base or an acid including Lewis acid.

Suitable bases may include inorganic bases and organic bases such as an alkali metal [e.g., sodium or potassium], hydroxide, carbonate or bicarbonate thereof, a trialkylamine [e.g., trimethylamine or triethylamine] or the like.

Suitable acids may include organic acids [e.g., formic acid, acetic acid, propionic acid, trichloroacetic acid or trifluoroacetic acid] and inorganic acids [e.g., hydrogen chloride, hydrochloric acid, hydrogen bromide, hydrobromic acid or sulfuric acid]. The elimination using Lewis acid such as trihaloacetic acid [e.g., trichloroacetic acid or trifluoroacetic acid] or the like is preferably carried out in the presence of a cation trapping agent [e.g., anisole or phenol].

The reaction is usually carried out in a solvent such as water, an alcohol [e.g., methanol or ethanol], methylene chloride, tetrahydrofuran, 1,2-dimethoxyethane, a mixture thereof or any other solvent which does not adversely influence the reaction. A liquid base or acid can be also used as a solvent.

The reaction may be usually carried out under cooling to warming since the reaction temperature is not critical.

Process A

A compound (II-4) can be prepared from a compound (III) according to a method described in Preparations 1 to 6, 8 to 13, 14 to 19, 20 to 25 or similar method thereto.

Process B

A compound (II-5) can be prepared by subjecting a compound (II-4) to hydrogenation. The hydrogenation can be carried out according to a method described in Preparation 7 or similar manner thereto.

Process C

A compound (II-2) can be prepared by subjecting a compound (IX) to hydroxylation. The hydroxylation can be carried out in accordance with a method described in Preparations 26, 27

A compound (II-2) can be prepared by subjecting a compound (IX) to hydroxylation. The hydroxylation can be carried out in accordance with a method described in Preparations 26, 27 or similar manner thereto.

The pharmaceutically acceptable salts of the compounds (I) as mentioned above may be prepared by treating the compound (I) with an appropriate base or acid in accordance with the conventional method.

The object compounds (I) of this invention and pharmaceutically acceptable salt thereof may exert pharmacological activities such as an inhibitory activity on platelet aggregation, vasodilating activity, antihypertensive activity or the like, which are believed to be $PGI_2$ agonist. Accordingly, they can be used for treating and/or preventing thrombosis, arterial obstruction (e.g., chronic arterial obstruction), cerebrovascular disease, gastric ulcer, hepatitis, hepatic insufficiency, hepatic cirrhosis, arteriosclerosis, ischemic heart disease, restenosis or ischemic complications after coronary angioplasty (e.g., PTCA or coronary stenting), hypertension, inflammation, autoimmune disease, heart failure, renal disease (e.g., renal failure or nephritis), diabetic complication (e.g., diabetic neuropathy, diabetic nephropathy or diabetic retinopathy), peripheral circulatory disturbance, and the like. Moreover, they can be used for protecting organs after transplantation or surgery.

Further, the object compounds (I) and pharmaceutically acceptable salts thereof can be also used as a component for organ preserving fluids and as an agent for inhibiting metastasis of cancer.

Still further, the object compounds (I) may be also useful for treating and/or preventing dermatosis (e.g., chilblain, bedsore or baldness).

The compounds (I) of the present invention have much advantages, such as stronger activity, more suitable half-life period, decreased adverse effect, or the like, compared to the known 4,5-diaryloxazole compounds shown in the prior arts.

In order to show the utility of the object compounds (I), pharmacological data of the representative compounds thereof are shown in the following.

Inhibition of Human Platelet Aggregation Induced by ADP

[I] Test Compound:
(1) Sodium {3-{[2-(4,5-diphenyloxazol-2-yl)-1-hydroxy-2-cyclohexen-1-yl]methyl}phenoxy}acetate,
(2) Sodium {3-{[(1S)-2-(4,5-diphenyloxazol-2-yl)-4-hydroxy-2-cyclohexen-1-yl]methyl}phenoxy}acetate,
(3) Sodium {3-{[(1S)-2-(4,5-diphenyloxazol-2-yl)-2,3-epoxy-1-cyclohexyl]methyl}phenoxy}acetate.

[II] Test Method

Human blood was collected from healthy volunteers and mixed with 1/10 volume of 3.8% sodium citrate solution, pH 7.4. The citrate blood was centrifuged at 150×g for 10 minutes and the platelet rich plasma (PRP) was removed. The remaining blood was centrifuged for a further 10 minutes at 1500×g to prepare the platelet poor plasma (PPP), which was used as a reference for platelet aggregation. Aggregation studies were carried out using HEMATRACER 801 (NBS, Japan), a 8 channel aggregometer. 25 µl of a solution of Test compound in Tris-acetate buffer pH 7.4 and 225 µl of PRP were mixed and stirred at 1000 rpm for 2 minutes at 37° C. Aggregation was induced by ADP (adenosin 5'-diphosphate) solution at the final concentration of 2.5 µM.

[III] Test result:

| Test Compound ($1.0 \times 10^{-7}$M) | Inhibition (%) |
| --- | --- |
| (1) | >90 |
| (2) | >90 |
| (3) | >90 |

The pharmaceutical composition of the present invention which contains the object compound (I) or a pharmaceutically acceptable salt thereof as an active ingredient can be used in the form of a pharmaceutical preparation, for example, in solid, semisolid or liquid form (e.g., tablet, pellet, troche, capsule, suppository, cream, ointment, aerosol, powder, solution, emulsion or suspension), which are suitable for rectal, pulmonary (nasal or buccal inhalation), nasal, ocular, external (topical), oral or parenteral (including subcutaneous, intravenous and intramuscular) administrations or insufflation.

The pharmaceutical composition of this invention may contain various organic or inorganic carrier materials which are conventionally used for pharmaceutical purpose, such as excipients (e.g., sucrose, starch, mannite, sorbit, lactose, glucose, cellulose, talc, calcium phosphate or calcium carbonate), binding agents (e.g., cellulose, methyl cellulose, hydroxypropylcellulose, polypropylpyrrolidone, gelatin, gum arabic, polyethyleneglycol, sucrose or starch), disintegrators (e.g., starch, carboxymethylcellulose, calcium salt of carboxymethylcellulose, hydroxypropylstarch, sodium glycol-starch, sodium bicarbonate, calcium phosphate or calcium citrate), lubricants (e.g., magnesium stearate, talc or sodium laurylsulfate), flavoring agents (e.g., citric acid, mentol, glycine or orange powders), preservatives (e.g., sodium benzoate, sodium bisulfite, methylparaben or propylparaben), stabilizers (e.g., citric acid, sodium citrate or acetic acid), suspending agents (e.g., methyl cellulose, polyvinylpyrrolidone or aluminum stearate), dispersing agents, aqueous diluting agents (e.g., water) and base waxes (e.g., cacao butter, polyethyleneglycol or white petrolatum).

The compound (I) may usually be administered with a unit dose of 0.01 mg/kg to 50 mg/kg, 1 to 4 times a day. However, the above dosage may be increased or decreased according to age, weight, conditions of the patient or the administering method.

Abbreviations used in this application are as follows:
THF:Tetrahydrofuran
EtOAc:Ethyl acetate
DMF:N,N-Dimethylformamide
DMSO:Dimethylsulfoxide
MeOH:Methyl alcohol
tBuOH:tertButyl alcohol
nBuLi:n-Butyllithium
AD-mix-α: reagent for Sharpless Asymmetric Dihydroxylation containing a chiral ligand hydroquinine 1,4-phthalazinediyl diether, $K_3Fe(CN)_6$, $K_2CO_3$ and $K_2OsO_4 \cdot 2H_2O$ AD-mix-β:reagent for Sharpless Asymmetric Dihydroxylation containing a chiral ligand hydroquinine 1,4-phthalazinediyl diether, $K_3Fe(CN)_6$, $K_2CO_3$ and $K_2OsO_4 \cdot 2H_2O$ The patents, patent applications and publications cited herein are incorporated by reference.

BEST MODE FOR CARRING THE INVENTION

The following Examples are given only for the purpose of illustrating the present invention in more detail.

Preparation 1

A solution of AD-mix-β (300 g) in a mixture of t-BuOH (1000 ml) and water (1000 ml) was stirred for 1 hour, and then methanesulfonamide (22 g) and 1-cyclohexen-1-ylmethyl 4-(methoxy)benzoate (53 g) were added to the solution at 0° C. After being stirred for 20 hours at the same temperature, the reaction mixture was added with sodium sulfite (120 g) and stirred for 30 minutes. The mixture was partitioned between EtOAc and water. The organic layer was washed with 1N-HCl solution, sat. $NaHCO_3$ solution and then brine(a saturated sodium chloride aqueous solution). Then it was dried over $MgSO_4$ and evaporated in vacuo. The residue was purified by crystallization from a mixture of diethyl ether and hexane to afford [(1R,2R)-1,2-(dihydroxy)-1-cyclohexyl]methyl 4-(methoxy)benzoate (35 g).

IR (Neat): 3300 $cm^{-1}$ NMR ($CDCl_3$, δ): 1.0–1.8(8H, m), 2.6(1H, s), 2.96(1H, d, J=4 Hz), 3.87(3H, s), 4.00(1H, d, J=11.6 Hz), 4.57(1H, d, J=11.6 Hz), 6.93(2H, d, J=8 Hz), 8.00(2H, d, J=8 Hz). MS m/z: 281 ($M^+$+1) HPLC: chiralcel OD, 10% isopropanol/hexane, 29.6 ml/min Preparation 2

To a solution of [(1R,2R)-1,2-(dihydroxy)-1-cyclohexyl] methyl 4-(methoxy)benzoate (30 g) in dichloromethane (300 ml) were added dimethoxypropnane (50 ml) and p-toluenesulphonic acid (0.3 g) at room temperature. After being stirred for 4 hours, the reaction mixture was evaporated in vacuo. The residue was diluted with EtOAc, and the mixture was washed with water and brine. After evaporating the solvent, the residue was dissolved in a mixture of MeOH (200 ml) and THF (100 ml), followed by addition of 1N-NaOH(160 ml) at room temperature. After stirring for 12 hours at room temperature, the mixture was evaporated to remove the solvent. The resultant was partitioned between EtOAc and water. The organic layer was washed with water and brine, and evaporated in vacuo. The residue was purified by chromatography on silica gel to give (3aR,7aR)-2,2-dimethyl-hexahydro-1,3-benzodioxol-3a-yl)methanol (14 g).

NMR ($CDCl_3$, δ):1.29(3H, s), 1.52(3H, s), 1.0–1.8(7H, m), 2.0–2.2(2H, m), 3.58(2H, d, J=8.0 Hz), 4.16(1H, m)

Preparation 3

To a solution of $(COCl)_2$ (9.8 ml) in $CH_2Cl_2$ (200 ml) was dropwise added DMSO (10.7 ml) at −78° C. After 10minutes, a solution of (3aR,7aR)-2,2-dimethyl-hexahydro-1,3-benzodioxol-3a-yl)methanol (14 g) in $CH_2Cl_2$(50 ml) was added to the above solution at the same temperature. After 10 minutes, the mixture was added with triethylamine (42 ml) and allowed to stand at room temperature. After evaporating the solvent, the resultant was partitioned between EtOAc and water. The organic layer was washed with water and brine, and evaporated in vacuo to give an aldehyde compound.

To a solution of 3-tertbutyldiphenylsilyloxyphenylbromide (33 g) in THF (300 ml) was added nBuLi (54 ml, 1.5N-solution in THF) at −78° C. After stirring for 1 hour, the above aldehyde compound (10 g) was added to the mixture at the same temperature. After stirring for 1 hour, the mixture was partitioned between EtOAc and water. The organic layer was washed with 1N-HCl solution, water and brine, and evaporated in vacuo. The residue was purified by chromatography on silica gel to give 3-[((3aR,7aR)-2,2-dimethyl-hexahydro-1,3-benzodioxol-3a-yl)hydroxymethyl]-1-(tertbutyldiphenylsilyloxy)benzene (16 g).

IR (Neat): 3070, 1600 $cm^{-1}$ NMR ($CDCl_3$, δ): 1.22(9H, s), 1.0–1.6(8H, m), 1.30(3H, s), 1.46(3H, s), 2.54(1H, d, J=8 Hz), 4.22(1H, m), 4.44(1H, d, J=8 Hz), 6.6–7.2(4H, m), 7.2–7.8(10H, m) MS m/z: 517 ($M^+$+1)

Preparation 4

To a solution of 3-[((3aR,7aR)-2,2-dimethyl-hexahydro-1,3-benzodioxol-3a-yl) hydroxymethyl]-1-(tertbutyldiphenyl-silyloxy)benzene (45 g) in $CH_2Cl_2$ (450 ml) were added phenyl chlorothionoformate (14.5 ml) and pyridine (18 ml) at 0° C. After being stirred for 12 hours at room temperature, the mixture was evaporated and the resultant was partitioned between EtOAc and water. The organic layer was washed with water, 1N-HCl solution, sat.$NaHCO_3$ solution and then brine. The solvent was evaporated in vacuo to give an oily residue. The residue was dissolved in toluene (400 ml) to which tributyltinhydride (50 ml) and 2,2'-azobis-(isobutyronitrile)(100 mg) were added. The mixture was refluxed for 4 hours under stirring and then purified by chromatography on silica gel to give an oily compound. The oily compound was dissolved in a mixture of MeOH (200 ml) and THF (100 ml), to which p-toluenesulphonic acid (200mg) was added at room temperature. The mixture was stirred for 12 hours and evaporated. The residue was partitioned between EtOAc and water. The organic layer was washed with water, sat. NaHCO$_3$ solution and then brine. The solvent was evaporated in vacuo to give (1R,2R)-1-[3-(tertbutyldiphenylsilyloxy)benzyl]-1,2-dihydroxycyclohexane (30 g).

IR (Neat): 3420, 1600 cm$^{-1}$ NMR (CDCl$_3$, δ):1.10(9H, s), 0.8–1.8(8H, m), 2.57(1H, d, J=12 Hz), 2.67(1H, d, J=12 Hz), 3.15(1H, m), 6.51(1H, m), 6.73(2H, m), 7.07(1H, t, J=8.0 Hz), 7.2–7.7(10H, m) MS m/z: 461 (M$^+$+1)

Preparation 5

To a solution of (COCl)$_2$ (3.4 ml) in CH$_2$Cl$_2$ (100 ml) was dropwise added DMSO (3.7 ml) at −78° C. After 10minutes, a solution of (1R,2R)-1-[3-(tertbutyldiphenylsilyloxy)benzyl]-1,2-dihydroxycyclohexane (12 g) in CH$_2$Cl$_2$(50 ml) was added to the above mixture at the same temperature. After 10 minutes, the mixture was added with triethylamine (15 ml) and allowed to stand at room temperature. After evaporating the solvent, the residue was partitioned between EtOAc and water. The organic layer was washed with water and brine. The organic solvent was evaporated in vacuo to give an oily compound. The oily compound was dissolved in DMF (50 ml) and then added with trimethylsilychloride (6.6 ml) and imidazole(7.0 g) at room temperature. After stirring for 5 hours, the mixture was partitioned between EtOAc and water. The organic solvent was evaporated in vacuo. The residue was purified by chromatography on silica gel to give (R)-1-[3-(tertbutyldiphenylsilyloxy)benzyl]-1-trimethylsilyoxy-2-cyclohexanone (1.15 g).

IR (Neat): 1720 cm$^{-1}$ NMR (CDCl$_3$, δ): 0.016(9H, s), 1.05(9H, s), 1.2–1.8(6H, m), 2.2–2.4(2H, m), 2.70(1H, d, J=13.6 Hz), 2.84(1H, d, J=13.6 Hz), 6.4–6.8(3H, m), 6.90 (1H, t, J=8 Hz), 7.2–7.8(10H, m) MS m/z: 531 (M$^+$+1)

Preparation 6

To a solution of (4,5-diphenyl)oxazole (17 g) in THF (100 ml) was added n-BuLi (57 ml, 1.6N-solution in hexane) at −78° C. After stirring for 30 minutes, a solution of (R)-1-[3-(tertbutyldiphenyl-silyloxy)benzyl]-1-trimethylsilyoxy-2-cyclohexanone (27 g) in THF (50 ml) was added to the above mixture at the same temperature. After stirring for 1 hour, the reaction mixture was partitioned between EtOAc and water. The organic layer was washed with 1N-HCl solution and brine. The organic solvent was evaporated in vacuo to give a residue. The residue was dissolved in toluene (100 ml) and then added with (methoxycarbonylsulfamoyl) triethyl-ammonium hydroxide, inner salt(20.4 g) at room temperature. After refluxing under stirring for 5 hours, the reaction mixture was evaporated in vacuo. The residue was purified by chromatography on silica gel to give (R)-2-(4,5-diphenyloxazol-2-yl)-1-trimethylsilyloxy-1-[3-(tertbutyldiphenylsiloxy)benzyl]-2-cyclohexene (36 g).

IR (Neat): 1600, 1585 cm$^{-1}$ NMR (CDCl$_3$, δ): 0.036(9H, s), 1.12(9H, s), 1.4–1.8(4H, m), 2.1–2.4(2H, m), 3.10(1H, d, J=13.4 Hz), 3.48(1H, d, J=13.4 Hz), 6.6–7.0(5H, m), 7.2–7.8 (10H, m) MS m/z: 735 (M$^+$+1)

Preparation 7

A mixture of (R)-2-(4,5-diphenyloxazol-2-yl)-1-trimethylsilyloxy-1-[3-(tertbutyldiphenylsiloxy)benzyl]-2-cyclohexene (24 g) and 10% Pd/C (10 g) in a mixture of MeOH (200 ml) and EtOAc (500 ml) was stirred under H$_2$ for 8 hours. The catalyst was filtered off and the filtrate was evaporated in vacuo. The residue was purified by chromatography on silica gel to give (1R, 2S)-2-(4,5-diphenyloxazol-2-yl)-1-trimethylsilyoxy-1-[3-(tertbutyldiphenylsiloxy)benzyl]cyclohexane (21 g).

IR (Neat): 1600, 1583 cm$^{-1}$ NMR (CDCl$_3$, δ): 1.08(9H, s), 1.0–2.0(8H, m), 2.63(1H, d, J=13.8 Hz), 2.71(1H, d J=13.8 Hz), 3.1(1H, m), 6.6–7.0(4H, m), 7.2–7.7(10H, m)

Preparation 8

[(1S,2S)-1,2-(Dihydroxy)-1-cyclohexyl]methyl 4-(methoxy)benzoate was obtained in the same manner as in Preparation 1 except using AD-mix-α instead of AD-mix-β.

IR (Neat): 3300 cm$^{-1}$ NMR (CDCl$_3$, δ): 1.0–1.8(8H, m), 2.6(1H, s), 2.96(1H, d, J=4 Hz), 3.87(3H, s), 4.00(1H, d, J=11.6 Hz), 4.57(1H, d, J=11.6 Hz), 6.93(2H, d, J=8 Hz), 8.00(2H, d, J=8 Hz)

MS m/z: 281 (M$^+$+1) HPLC: chiralcel OD, 10% isopropanol/hexane, 19.9 ml/min

Preparation 9

((3aS,7aS)-2,2-Dimethyl-hexahydro-1,3-benzodioxol-3a-yl)methanol (14 g) was obtained in the same manner as in Preparation 2.

NMR (CDCl$_3$, δ): 1.29(3H, s), 1.52(3H, s), 1.0–1.8(7H, m), 2.0–2.2(2H, m), 3.58(2H, d, J=8.0 Hz), 4.16(1H, m)

Preparation 10

3-[((3aS,7aS)-2,2-Dimethyl-hexahydro-1,3-benzodioxol-3a-yl)hydroxymethyl]-1-(tertbutyldiphenylsilyloxy)benzene was obtained in the same manner as in Preparation 3.

IR (Neat): 3070, 1600 cm$^{-1}$ NMR (CDCl$_3$, δ): 1.22(9H, s), 1.0–1.6(8H, m), 1.30(3H, s), 1.46(3H, s), 2.54(1H, d, J=8 Hz, 4.22(1H, m), 4.44(1H, d, J=8 Hz), 6.6–7.2(4H, m), 7.2–7.8(10H, m) MS m/z: 517 (M$^+$+1)

Preparation 11

(1S,2S)-1-[3-(Tertbutyldiphenylsilyloxy)benzyl]- 1,2-dihydroxycyclohexane was obtained in the same manner as in Preparation 4.

IR (Neat):3420, 1600 cm$^{-1}$ NMR (CDCl$_3$, δ): 1.10(9H, s), 0.8–1.8(8H, m), 2.57(1H, d, J=12 Hz), 2.67(1H, d, J=12 Hz), 3.15(1H, m), 6.51(1H, m), 6.73(2H, m), 7.07(1H, t, J=8.0 Hz), 7.2–7.7(1H, m) MS m/z: 461(M$^+$+1)

Preparation 12

(S)-1-[3-(Tertbutyldiphenylsilyloxy)benzyl]-1-trimethylsilyoxy-2-cyclohexanone was obtained in the same manner as in Preparation 5.

IR (Neat): 1720 cm$^{-1}$ NMR (CDCl$_3$, δ): 0.016(9H, s), 1.05(9H, s), 1.2–1.8(6H, m), 2.2–2.4(2H, m), 2.70(1H, d, J=13.6 Hz), 2.84(1H, d, J=13.6 Hz), 6.4–6.8(3H, m), 6.90 (1H, t, J=8 Hz), 7.2–7.8(10H, m) MS m/z: 531 (M$^+$+1)

Preparation 13

(S)-2-(4,5-Diphenyloxazol-2-yl)-1-trimethylsilyloxy-1-[3-(tertbutyldiphenylsiloxy)benzyl]-2-cyclohexene was obtained in the same manner as in Preparation 6.

IR (Neat): 1600, 1585 cm$^{-1}$ NMR (CDCl$_3$, δ): 0.036(9H, s), 1.12(9H, s), 1.4–1.8(4H, m), 2.1-14 2.4(2H, m), 3.10(1H, d, J=13.4 Hz), 3.48(1H, d, J=13.4 Hz), 6.6–7.0(5H, m), 7.2–7.8(10H, m) MS m/z: 735 (M$^+$+1)

Preparation 14

[(1S,2S)-1,2-(Dihydroxy)-1-cyclopentyl]methyl 4-(methoxy)benzoate was obtained in the same manner as in Preparation 8.

IR (Neat): 3300 cm$^{-1}$ NMR (CDCl$_3$, δ): 1.0–1.8(6H, m), 2.69(1H, d, J=5.2 Hz), 3.07(1H, s), 3.86(3H, s), 4.22(1H, d, J=11.6 Hz), 4.35(1H, d, J=11.6 Hz), 6.91(2H, d, J=8 Hz), 8.00(2H, d, J=8 Hz) MS m/z: 267 (M$^+$+1)

Preparation 15

((3aS,6aS)-2,2-Dimethyl-tetrahydro-4H-cyclopenta-1,3-dioxol-3a-yl)methanol was obtained in the same manner as in Preparation 2.

IR (Neat): 3400 cm$^{-1}$ NMR (CDCl$_3$, δ):1.39(3H, s), 1.48(3H, s), 1.0–2.0(7H, m), 3.5–3.8(2H, m), 4.44(1H, d, J=4.0 Hz) MS m/z: 173 (M$^+$+1)

Preparation 16

3-[((3aS, 6aS)-2,2-Dimethyl-tetrahydro-4H-cyclopenta-1,3-dioxol-3a-yl) hydrorymethyl]-1-(tertbu tyldiphenyl silyloxy) benzene was obtained in the same manner as in Preparation 3.

IR (Neat): 3400, 1600 cm$^{-1}$ NMR (CDCl$_3$, δ): 1.22(91 1, s), 1.0–1.8(61 1, m), 1.32(3H, s), 1.41(3H, s), 4.2–4.6(2H, m), 6.6–7.2(4H1, m), 7.2–7.8(10H, m) MS m/z: 503 (M$^+$+1)

Preparation 17

(1S,2S)-1-[3-(Tertbutyldiphenylsilyloxy)benzyl]-1,2-dihydroxycyclopentane was obtained in the same manner as in Preparation 4.

IR (Neat): 3300, 1600 cm$^{-1}$NMR (CDCl$_3$, δ): 1.09(9H, s), 0.8–1.8(6H, m), 2.57(2H, s), 3.59(1H, m), 6.52(1H, m), 6.7–6.9(2H, m), 7.06(1H, t, J=8 Hz), 7.2–7.7(10H, m) MS m/z: 445 (M$^+$+1)

Preparation 18

(S)-1-[3-(Tertbutyldiphenylsilyloxy)benzyl]-1-trimethylsilyoxy-2-cyclopentanone was obtained in the same manner as in Preparation 5.

IR (Neat): 1749 cm$^{-1}$ NMR (CDCl:$_3$, δ): 0.016(9H, s), 1.04(9H, s), 1.2–2.0(6H, m), 2.56(2H, s), 6.4–6.8(3H, m), 6.93(1H, t, J=8 Hz), 7.2–7.8(10H, m) MS m/z: 517 (M$^+$+1)

Preparation 19

(S)-2-(4,5-Diphenyloxazol-2-yl) -1-trimethylsilyloxy-1-[3-(tertbutyldiphenylsiloxy)benzyl]-2-cyclopentene was obtained in the same manner as in Preparation 6.

IR (Neat): 1600, 1585 cm$^{-1}$ NMR (CDCl$_3$, δ): 0.036(9H, s), 1.09(9H, s), 1.4–2.2(4H, m), 2.9–3.3(2H, m), 6.4–7.0 (4H, m), 7.10(1H, t, J=8 Hz) 7.2–7.8(10H, m) MS m/z: 721 (M$^+$+1)

Preparation 20

[(1R,2R)-1,2-(Dihydroxy)-1-cyclopentyl]methyl 4-(methoxy)benzoate was obtained in the same manner as in Preparation 1.

IR (Neat): 3300 cm$^{-1}$ NMR (CDCl$_3$, δ): 1.0–1.8(6H, m), 2.69(1H, d, J=5.2 Hz), 3.07(1H, s), 3.86(3H, s), 4.22(1H, d, J=11.6 Hz), 4.35(1H, d, J=11.6 Hz), 6.91(2H, d, J=8 Hz), 8.00(2H, d, J=8 Hz) MS m/z: 267 (M$^+$+1) HPLC: chiralcel OD, 10% isopropanol/hexane, 8.3 ml/min Preparation 21

(3aR,6aR)-(2,2-Dimethyl-tetrahydro-4H-cyclopenta-1,3-dioxol-3a-yl)methanol was obtained in the same manner as in Preparation 2.

IR (Neat): 3400 cm$^{-1}$ NMR (CDCl$_3$, δ): 1.39(3H, s), 1.48(3H, s), 1.0–2.0(7H, m), 3.5–3.8(2H, m), 4.44(1H, d, J=4.0 Hz) MS m/z: 173(M$^+$+1)

Preparation 22

3-[((3aR, 6aR)-2,2-Dimethyl-tetrahydro-4H-cyclopenta-1,3-dioxol-3a-yl)hydroxymethyl-1-tertbutyldiphenylsilyloxy-benzene was obtained in the same manner as in Preparation 3.

IR (Neat): 3400, 1600 cm$^{-1}$ NMR (CDCl$_3$, δ): 1.22(9H, s), 1.0–1.8(6H, m), 1.32(3H, s), 1.41(3H, s), 4.2–4.6(2H, m), 6.6–7.2(4H, m), 7.2–7.8(10H, m) MS m/z: 503 (M$^+$+1)

Preparation 23

(1R,2R)-1-[3-(Tertbutyldiphenylsilyloxy)benzyl]-1,2-dihydroxycyclopentane was obtained in the same manner as in Preparation 4.

IR (Neat): 3300, 1600 cm$^{-1}$NMR (CDCl$_3$, δ): 1.09(9H, s), 0.8–1.8(6H, m), 2.57(2H, s), 3.59(1H, m), 6.52(1H, m), 6.7–6.9(2H, m), 7.06(1H, t, J=8 Hz), 7.2–7.7(10H, m) MS m/z: 445 (M$^+$+1)

Preparation 24

(R)-1-[3-(Tertbutyldiphenylsilyloxy) benzyl]-1-trimethylsilyoxy-2-cyclopentanone was obtained in the same manner as in Preparation 5.

IR (Neat): 1749 cm$^{-1}$

NMR (CDCl$_3$, δ): 0.016(9H, s), 1.04(9H, s), 1.2–2.0(6H, m), 2.56(2H, s), 6.4–6.8(3H, m), 6.93(1H, t, J=8 Hz), 7.2–7.8(10H, m) MS m/z: 517 (M$^+$+1)

Preparation 25

(R)-2-(4,5-Diphenyloxazol-2-yl)-1-trimethylsilyloxy-1-[3-(tertbutyldiphenylsiloxy)benzyl]-2-cyclopentene was obtained in the same manner as in Preparation 6.

IR (Neat): 1600, 1585 cm$^{-1}$ NMR (CDCl$_3$, δ): 0.036(9H, s), 1.09(9H, s), 1.4–2.2(4H, m), 2.9–3.3(2H, m), 6.4–7.0 (4H, m), 7.10(1H, t, J=8 Hz) 7.2–7.8(10H, m) MS m/z: 721 (M$^+$+1)

Preparation 26

(1S,2R,3S)-2-(4,5-Diphenyloxazol-2-yl)-2,3-dihydroxy-1-[3-(tertbutyldiphenylsiloxy)benzyl]cyclohexane was obtained in the same manner as in Preparation 8.

IR (Neat):3600 cm$^{-1}$ NMR (CDCl$_3$, δ): 1.06(9H, s), 1.2–2.4(9H, m), 3.98(1H, m), 6.4–6.7(3H, m), 6.88(1H, t, J=8 Hz), 7.2–7.7(10H, m) Ms m/z: 680 (M$^+$–17)

Preparation 27

(1S,2S,3R)-2-(4,5-Diphenyloxa7,ol-2-yl)-2,3-dihydroxy-1-[3-(tertbutyldiphenylsiloxy)benzyl]cyclohexane was obtained in the same manner as in Preparation 1.

IR (Neat): 3600 cm$^{-1}$ NMR (CDCl$_3$, δ): 1.08(9H, s), 1.2–2.4(9H, m), 4.32(1H, m), 6.4–6.7(3H, m), 6.938(1H, t, J=8 Hz), 7.2–7.7(10H, m) Ms m/z: 680 (M$^+$–17)

EXAMPLE 1

A solution of ethyl (S)-{3-{[2-(4,5-diphenyloxazol-2-yl)-2-cyclohexen-1-yl]methyl}phenoxy}acetate (380 mg) (prepared by a method described in WO 95/17393) and selenium dioxide (SeO$_2$) (170 mg) in dichloromethane (230 ml) was refluxed for 2 hours under stirring. The mixture was filtered and the filtrate was evaporated. The residue was purified by chromatography on silica gel to give ethyl {3-{[2-(4,5-diphenyloxazole-2-yl)-1-hydroxy-2-cyclohexen-1-yl]-methyl}phenoxy}acetate (60 mg) as a first fraction and ethyl {3-{[(1S)-2-(4,5-diphenyloxazol-2-yl)-4-hydroxy-2-cyclohexen-1-yl]methyl}phenoxy}acetate (80 mg) as a second fraction.

First fraction:

IR (Neat): 3400, 1758 cm$^{-1}$NMR (CDCl$_3$, δ): 1.28 (3H, t, J=7.0 Hz), 1.4–2.0 (5H, m), 2.2–2.4 (2H, m), 3.05 (1H, d, J=13.6 Hz), 3.40 (1H, d, J=13.6 Hz), 4.26 (2H, q, J=7.0 Hz), 4.51 (2H, s), 6.70 (1H, d, J=8 Hz), 6.8–7.0 (3H, m), 7.15 (1H, t, J=8 Hz), 7.2–7.8 (10H, m) MS m/z: 510 (M$^+$+1)

Second fraction:

IR (Neat):3400, 1758 cm$^{-1}$ NMR (CDCl$_3$, δ): 1.25 (3H, t, J=7.0 Hz), 1.4–2.0 (5H, m), 2.47 (1H, dd, J=10.0, 12.6 Hz), 3.1 (1H, m), 3.29 (1H, dd, J=3.2, 12.6 Hz), 4.24 (2H, q, J=7.0 Hz), 4.39 (1H, m), 4.59 (2H, s), 6.73 (1H, d, J=8 Hz), 6.8–7.0 (3H, m), 7.21 (1H, t, J=8 Hz), 7.2–7.8 (10H, m) MS m/z: 510 (M$^+$+1)

EXAMPLE 2

A solution of ethyl (S)-{3-{[2-(4,5-diphenyloxazol-2-yl)-2-cyclohexen-1-yl]methyl}phenoxy}acetate (800 mg) and m-chloroperbenzoic acid (600 mg) in dichloromethane (20 ml) was stirred for 2 hours at room temperature. The mixture was diluted with EtOAc and washed with water and brine. Then, it was dried over MgSO$_4$ and evaporated in vacuo. The residue was purified by chromatography on silica gel to give ethyl {3-{[(1S)-2-(4,5-diphenyloxazol-2-yl) -2,3-epoxy-1-cyclohexyl]methyl}phenoxy}-acetate (400 mg).

IR (Neat): 1760 cm$^{-1}$ NMR (CDCl$_3$, δ): 1.28 (3H, t, J=7.0 Hz), 1.4–2.0 (6H,m), 2.59 (1H, dd, J=9.0, 12.8 Hz), 2.9–3.1 (1H, m), 3.22 (1H, dd, J=5.0, 12.8 Hz), 4.26 (2H, q, J=7.0 Hz), 4.51 (2H, s), 6.66 (1H, d, J=8 Hz), 6.7–7.0 (2H, m), 7.16 (1H, t, J=8 Hz), 7.2–7.8 (10H, m) MS m/z: 510 (M$^+$+1)

EXAMPLE 3

A solution of ethyl (S)-{$^3$-{[2-(4,5-diphenytoxazol-2-yl)-2-cyclopenten-1-yl]methyl}phenoxy}acetate (1.0 g)

(prepared by a method described in WO 95/17393) and m-chloroperbenzoic acid (0.45 g) in dichloromethane (20 ml) was stirred for 2 hours at room temperature. The mixture was diluted with EtOAc and washed with water and brine. Then it was dried over $MgSO_4$ and evaporated in vacuo. The residue was purified by chromatography on silica gel to give ethyl {3-{[(1S)-2-(4,5-diphenyloxazol-2-yl)-2,3-epoxy-1-cyclopentyl]methyl}phenoxy}-acetate (400mg).

IR (Neat): 1760 $cm^{-1}$ NMR ($CDCl_3$, δ): 1.28(3H, t, J=7.0 Hz), 1.4–2.0(4H, m), 2.4–3.2(3H, m), 4.26(2H, q, J=7.0 Hz), 4.51(2H, s), 6.6–7.1(4H, m), 7.2–7.8(10H, m) MS m/z: 496($M^+$+1)

EXAMPLE 4

To a solution of (1S,2R,3S)-2-(4,5-diphenyloxazol-2-yl)-2,3-dihydroxy-1-[3-(tertbutyldiphenylsiloxy)benzyl] cyclohexane (8.7 g) in $CH_2Cl_2$ (100 ml) were added orthoacetic acid trimethyl ester (2.8 ml) and p-toluenesulfonic acid (150 mg) at room temperature under $N_2$ gas. After being stirred for 30 minutes, the mixture was evaporated in vacuo. The residue was diluted with $CH_2Cl_2$ (100 ml), followed by addition of acetylbromide (3.0 ml) at 0° C. under $N_2$ gas. After being stirred for 2 hours at room temperature, the mixture was evaporated in vacuo. The residue was diluted with MeOH (100 ml) and added with $K_2CO_3$ (5 g) at room temperature. The mixture was stirred for 2 hours at the same temperature and then partitioned between EtOAc and water. The organic layer was washed with 1N-HCl solution, water, sat. $NaHCO_3$ solution and brine. The organic solvent was evaporated in vacuo. The residue was purified by chromatography on silica gel to give an oily compound. The oily compound was dissolved in THF (50 ml), followed by addition of tetrabutylammonium fluoride (15 ml, 1M solution in THF) at room temperature. After being stirred for 4 hours, the mixture was diluted with EtOAc. The mixture was washed with 1N-HCl solution and brine and evaporated. The residue was dissolved in DMF (50 ml), followed by addition of $K_2CO_3$ (5 g) and ethyl bromoacetate (2.0 ml) at room temperature. The mixture was stirred for 2 hours at the same temperature and partitioned between EtOAc and water. The organic layer was washed with water and brine and evaporated in vacuo. The residue was purified by chromatography on silica gel to give ethyl {3-{[(1S,2R,3S)-2-(4,5-diphenyloxazol-2-yl)-2,3-epoxy-1-cyclohexyl]methyl}phenoxy}acetate (4.3 g).

IR (Neat): 1760 $cm^{-1}$ NMR ($CDCl_3$, δ): 1.28(3H, t, J=7.0 Hz), 1.4–2.0(6H, m), 2.59(1H, dd, J=9.0, 12.8 Hz), 2.9–3.1 (1H, m), 3.22 (1H, dd, J=5.0, 12.8 Hz), 3.76(1H, m), 4.22(2H, q, J=7.0 Hz), 4.51(2H, s), 6.66(1H, d, J=8 Hz), 6.7–7.0(2H, m), 7.16(1H, t, J=8 Hz), 7.2–7.8(10H, m) MS m/z: 510($M^+$+1)

EXAMPLE 5

Ethyl {3-{[(1S,2S,3R)-2-(4,5-diphenyloxazol-2-yl)-2,3-epoxy-1-cyclohexyl]methyl}phenoxy}acetate was obtained in the same manner as in Example 4.

IR (Neat):1760 $cm^{-1}$ NMR ($CDCl_3$, δ): 1.28(3H, t, J=7.0 Hz), 1.4–2.2(6H, m), 2.65(1H, dd, J=12 Hz, 14 Hz), 2.9–3.1 (2H, m), 3.98(1H, m), 4.22(2H, q, J=7.0 Hz), 4.50(2H, s), 6.66(1H, d, J=8 Hz), 6.7–6.9(2H, m), 7.16(1H, t, J=8 Hz), 7.2–7.8(10H, m) MS m/z: 510 ($M^+$+1)

EXAMPLE 6

To a solution of (R)-2-(4,5-diphenyloxazol-2-yl)-1-trimethylsilyloxy-1-[3-(tertbutyldiphenylsiloxy)benzyl]-2-cyclohexene (10 g) in THF (50 ml) was added tetrabutylammonium fluoride (41 ml, 1M solution in THF) at room temperature. After being stirred for 4 hours, the mixture was diluted with EtOAc. The mixture was washed with 1N-HCl solution and brine and evaporated. The residue was dissolved in DMF (50 ml), followed by addition of $K_2CO_3$ (5 g) and ethyl bromoacetate (2.0 ml) at room temperature. The mixture was stirred for 2 hours at the same temperature and partitioned between EtOAc and water. The organic layer was washed with water and brine and evaporated in vacuo. The residue was purified by chromatography on silica gel to give ethyl (R)-{3-{[2-(4,5-diphenyloxazole-2-yl)-1-hydroxy-2-cyclohexen-1-yl]methyl}phenoxy}-acetate (5.3 g).

IR (Neat): 3400, 1750 $cm^{-1}$ NMR ($CDCl_3$, δ) 1.25(3H, t, J=8 Hz), 1.6–2.0(4H, m), 2.2–2.4(2H, m), 3.05(1H, d, J=14 Hz), 3.40(1H, d, J=14 Hz), 4.25(2H, q, J=8 Hz), 4.51 (2H, s), 5.63(1H, s), 6.6–7.0(4H, m), 7.19(1H, t, J=8 Hz), 7.2–7.8 (10H, m) MS m/z: 510($M^+$+1) HPLC: chiralcel AD, 10% isopropanol/hexane, 11.3 ml/min

EXAMPLE 7

Ethyl {3-{[(1R,2S)-2-(4,5-diphenyloxazole-2-yl)-1-hydroxy-1-cyclohexyl]methyl}phenoxy}acetate was obtained in the same manner as in Example 6.

IR (Neat): 3300, 1735 $cm^{-1}$NMR ($CDCl_3$, δ): 1.25(3H, t, J=8 Hz), 1.3–2.2(7H, m), 2.2–2.4(1H, m), 2.80(1H, d, J=14 Hz), 2.90(1H, d, J=14 Hz), 3.13 (1H, dd, J=4.0, 11 Hz), 3.79(1H, br.s), 4.25(2H, q, J=8 Hz), 4.48 (2H, s), 6.6–6.9 (3H, m), 7.16(1H, t, J=8 Hz), 7.2–7.8(10H, m) MS m/z: 512 ($M^+$+1)

EXAMPLE 8

Ethyl (S)-{3-{[2-(4,5-diphenyloxazole-2-yl)-1-hydroxy-2-cyclohexen-1-yl]methyl}phenoxy}acetate was obtained in the same manner as in Example 6.

IR (Neat): 3400, 1750 $cm^{-1}$ NMR ($CDCl_3$, δ): 1.25(3H, t, J=8 Hz), 1.6–2.0(4H, m), 2.2–2.4(2H, m), 3.05(1H, d, J=14 Hz), 3.40(1H, d, J=14 Hz), 4.25(2H, q, J=8 Hz), 4.51 (2H, s), 5.63(1H, s), 6.6–7.0(4H, m), 7.19(1H, t, J=8 Hz), 7.2–7.8(10H, m) MS m/z: 510 ($M^+$+1)

EXAMPLE 9

Ethyl (S)-{3-{[2-(4,5-diphenyloxazole-2-yl)-1-hydroxy-2-cyclopenten-1-yl]methyl}phenoxy}acetate was obtained in the same manner as in Example 6.

IR (Neat): 3400, 1750 $cm^{-1}$ NMR ($CDCl_3$, δ): 1.25(3H, t, J=8 Hz), 1.6–2.5(4H, m), 3.1–3.3(2H, m), 4.25(2H, q, J=8 Hz), 4.54 (2H, s), 5.63(1H, s), 6.5–7.0(4H, m), 7.19(1H, t, J=8 Hz), 7.2–7.8(10H, m) MS m/z: 496($M^+$+1)

EXAMPLE 10

Ethyl (R)-{3-{[2-(4,5-diphenyloxazole-2-yl)-1-hydroxy-2-cyclopenten-1-yl]methyl}phenoxy}acetate was obtained in the same manner as in Example 6.

IR (Neat): 3400, 1750 $cm^{-1}$ NMR ($CDCl_3$, δ): 1.25(3H, t, J=8 Hz), 1.6–2.5(4H, m), 3.1–3.3(2H, m), 4.25(2H, q, J=8 Hz), 4.54 (2H, s), 5.63(1H, s), 6.5–7.0(4H, m), 7.19(1H, t, J=8 Hz), 7.2–7.8(10H, m) MS m/z: 496 ($M^+$+1)

EXAMPLE 11

Ethyl {3-{[(1R,5S)-2-(4,5-diphenyloxazole-2-yl)-5-hydroxy-2-cyclohexen-1-yl]methyl}phenoxy}acetate was obtained in the same manner as in Example 6.

IR (Neat):3400, 1750 $cm^{-1}$ NMR ($CDCl_3$, δ): 1.25(3H, t, J=8 Hz), 1.5–3.0(7H, m), 4.25(2H, q, J=8 Hz), 4.51 (2H, s), 6.7–7.0(4H, m), 7.2–7.8(11H, m) MS m/z: 510 ($M^+$+1)

EXAMPLE 12

Ethyl {3-{[(1R,5R)-2-(4,5-diphenyloxazole-2-yl)-5-hydroxy-2-cyclohexen-1-yl]methyl}phenoxy}acetate was obtained in the same manner as in Example 6.

IR (Neat):3400, 1750 cm$^{-1}$ NMR (CDCl$_3$, δ): 1.25(3H, t, J=8 Hz), 1.5–2.2(4H, m), 2.4–2.8(2H, m), 3.32(1H, m), 4.25(2H, q, J=8 Hz), 4.60 (2H, s), 6.7–7.0(4H, m), 7.2–7.8 (11H, m) MS m/z: 510 (M$^+$+1)

EXAMPLE 13

Ethyl {3-{[2-(4,5-diphenyloxazole-2-yl)-2-cyclohexen-1-yl]-hydroxymethyl}phenoxy}acetate was obtained in the same manner as in Example 6.

IR (Neat):3400, 1750 cm$^{-1}$ NMR (CDCl$_3$, δ): 1.25(3H, t, J=8 Hz), 1.2–1.9(4H, m), 2.2–2.6(2H, m), 3.2(1H, m), 4.25(2H, q, J=8 Hz), 4.60 (2H, s), 6.9–7.2(4H, m), 7.2–7.8 (11H, m) MS m/z: 510 (M$^+$+1)

EXAMPLE 14

Ethyl {3-{[2-(4,5-diphenyloxazole-2-yl)-1-cyclohexen-1-yl]-hydroxymethyl}phenoxy}acetate was obtained in the same manner as in Example 6.

IR (Neat): 3400, 1750 cm$^{-1}$ NMR (CDCl$_3$, δ): 1.25(3H, t, J=8 Hz), 1.4–2.0(4H, m), 2.0–2.8(4H, m), 4.25(2H, q, J=8 Hz), 4.58 (2H, s), 6.7–7.1(3H, m), 7.0–7.8(11H, m) MS m/z: 510(M$^+$+1)

EXAMPLE 15

To a solution of ethyl {3-{[2-(4,5-diphenyloxazole-2-yl)-1-hydroxy-2-cyclohexen-1-yl]methyl}phenoxy}acetate (60 mg) in ethanol (5 ml) was added 1N-NaOH solution (0.12 ml) at room temperature. After being stirred for 6 hours, the mixture was evaporated. The residue was added with diethyl ether. The resulting solid was collected by filtration to give sodium {3-{[2-(4,5-diphenyloxazol-2-yl)-1-hydroxy-2-cyclohexen-1-yl]methyl}phenoxy}acetate (34 mg).

IR (KBr): 3500, 1635 cm$^{-1}$ NMR (DMSO-d$_6$, δ): 1.4–1.9 (4H, m), 2.1–2.3 (2H, m), 3.99 (2H, s), 6.5–6.7 (3H, m), 6.8 (1H, m), 7.0 (1H, m), 7.3–7.8 (10H, m) MS m/z: 504 (M$^+$+1)

EXAMPLE 16(1)

The following compounds in (1) and (2) were obtained according to a similar manner to that of Example 15.
(1) Sodium {3-{[(1S)-2-(4,5-diphenyloxazol-2-yl)-4-hydroxy-2-cyclohexen-1-yl]methyl}phenoxy}acetate IR (KBr):3500, 1635 cm$^{-1}$ NMR (DMSO-d$_6$, δ): 1.3–2.0 (4H, m), 2.9–3.2 (2H; m), 4.09 (2H, s), 4.21 (1H, m), 6.6–6.8 (4H, m), 7.1 (1H, m), 7.3–7.8 (10H, m) MS m/z: 504 (M$^+$+1)
(2) Sodium {3-{[(1S)-2-(4,5-diphenyloxazol-2-yl)-2,3-epoxy-1-cyclohexyl]methyl}phenoxy}acetate IR (KBr): 1635 cm$^{-1}$ NMR (DMSO-d$_6$, δ): 1.2–1.8 (5H, m), 1.9–2.1 (2H, m), 3.0–3.2 (2H, m), 3.81 (1H, s), 4.04 (2H, s), 6.59 (1H, d, J=8 Hz), 6.6–6.8 (2H, m), 7.09 (1H, t, J=8 Hz), 7.3–7.8 (10H, m) MS m/z: 504 (M$^+$+1)

EXAMPLE 16(3)

To a solution of ethyl (R)-{3-{[2-(4,5-diphenyloxazole-2-yl)-1-hydroxy-2-cyclohexen-1-yl]methyl}phenoxy}acetate (7.8 g) in a mixture of ethanol (50 ml) and THF (50 ml) was added 1N-NaOH solution (15.3 ml) at room temperature. After being stirred for 4 hours at the same temperature, the mixture was evaporated. The residue was washed with diethyl ether to afford sodium (R)-{3-{[2-(4,5-diphenyloxazol-2-yl)-1-hydroxy-2-cyclohexen-1-yl]methyl}-phenoxy}acetate(6.7 g).

IR (Neat) ; 3500–3300, 1650 cm$^{-1}$ NMR (DMSO-d$_6$, δ); 1.5–1.9(4H, m), 2.2(2H, m), 3.0–3.4(2H, m), 4.025(2H, s), 5.08(1H, br.s), 6.4–6.7(3H, m), 6.86(1H, m), 7.05(1H, t, J=8 Hz), 7.2–7.8(10H, m) MS m/z; 504 (M$^+$+1)

EXAMPLE 16

The following compounds in (4) to (14) were obtained according to a similar manner to that of Example 16(3).
(4) Sodium {3-{[(1R,2S)-2-(4,5-diphenyloxazol-2-yl)-1-hydroxy-1-cyclohexyl]methyl}phenoxy}acetate IR (Neat): 3500–3300, 1650 cm$^{-1}$NMR (DMSO-d$_6$, δ): 1.0–2.0(8H, m), 2.72(1H, d, J=13.6 Hz), 2.82(1H, d, J=13.6 Hz), 3.03(1H, m), 4.05(2H, s), 4.69(1H, s), 6.5–6.8(3H, m), 7.03(1H, t, J=8 Hz), 7.2–7.6(10H, m) MS m/z: 506 (M$^+$+1)
(5) Sodium (S)-{3-{[2-(4,5-diphenyloxazol-2-yl)-1-hydroxy-2-cyclohexen-1-yl]methyl}phenoxy}acetate IR (Neat):3500–3300, 1650 cm$^{-1}$ NMR (DMSO-d$_6$, δ): 1.5–1.9(4H, m), 2.2(2H, m), 3.0–3.4(2H, m), 4.025(2H, s), 5.08(1H, br.s), 6.4–6.7(3H, m), 6.86(1H, m), 7.05(1H, t, J=8 Hz), 7.2–7.8(10H, m) MS m/z: 504 (M$^+$+1)
(6) Sodium (S)-{3-{[2-(4,5-diphenyloxazol-2-yl)-1-hydroxy-2-cyclopenten-1-yl]methyl}phenoxy}acetate IR (Neat):3500–3300, 1650 cm$^{-1}$ NMR (DMSO-d$_6$, δ): 1.5–1.9(4H, m), 4.14(2H, s), 6.4–6.8(4H, m), 7.04(1H, t, J=8 Hz), 7.2–7.8(10H, m) MS m/z: 490 (M$^+$+1)
(7) Sodium (R)-{3-{[2-(4,5-diphenyloxazol-2-yl)-1-hydroxy-2-cyclopenten-1-yl]methyl}phenoxy}acetate IR (Neat): 3500–3300, 1650 cm$^{-1}$ NMR (DMSO-d$_6$, δ): 1.5–1.9(4H, m), 4.14(2H, s), 6.4–6.8(4H, m), 7.04(1H, t, J=8 Hz), 7.2–7.8(10H, m) MS m/z: 490 (M$^+$+1)
(8) Sodium {3-{[(1S,2R,3S)-2-(4,5-diphenyloxazol-2-yl)-2,3-epoxy-1-cyclohexyl]methyl}phenoxy}acetate IR (KBr): 1635 cm$^{-1}$ NMR (DMSO-d$_6$, δ): 1.2–2.1(6H, m), 3.0–3.2(2H, m), 3.81(1H, s), 4.07(2H, s), 6.59(1H, d, J=8 Hz), 6.6–6.8(2H, m), 7.09 (1H, t, J=8 Hz), 7.3–7.8(10H, m) MS m/z: 504(M$^+$+1)
(9) Sodium {[3-{[(1S,2S,3R)-2-(4,5-diphenyloxazol-2-yl)-2,3-epoxy-1-cyclohexyl]methyl}phenoxy}acetate IR (KBr): 1635 cm$^{-1}$NMR (DMSO-d$_6$, δ): 1.2–2.1(6H, m), 2.6–3.0(3H, m), 3.95(1H, m), 4.02(2H, s), 6.5–6.8(3H, m), 7.08 (1H, t, J=8 Hz), 7.3–7.8(10H, m) MS m/z: 504 (M$^+$+1)
(10) Sodium {3-{[(1S)-2-(4,5-diphenyloxazol-2-yl)-2,3-epoxy-1-cyclopentyl]methyl}phenoxy}acetate IR (KBr): 1635 cm$^{-1}$ NMR (DMSO-d$_6$, δ): 1.2–2.0(4H, m), 2.7–3.1(2H, m), 3.81(1H, s), 4.05 and 4.08(2H, each s), 6.4–7.0(3H, m), 7.0–7.2(1H, m), 7.3–7.8(10H, m) MS m/z: 490 (M$^+$+1)
(11) Sodium {3-{[(1R,5S)-2-(4,5-diphenyloxazol-2-yl)-5-hydroxy-2-cyclohexen-1-yl]methyl}phenoxy}acetate IR (Neat): 3500–3300, 1650 cm$^{-1}$ NMR (DMSO-d$_6$, δ): 1.5–1.9(4H, m), 4.05(2H, s), 6.5–6.8(4H, m), 7.0–7.8(11H, m) MS m/z: 504(M$^+$+1)
(12) Sodium {3-{[(1R,5R)-2-(4,5-diphenyloxazol-2-yl)-5-hydroxy-2-cyclohexen-1-yl]methyl}phenoxy}acetatc IR (Neat): 3500–3300, 1650 cm$^{-1}$ NMR (DMSO-d$_6$, δ): 1.5–1.9(4H, m), 3.0–3.4(3H, m), 4.13(2H, s), 6.5–6.8(4H, m), 7.0–7.8(11H, m) MS m/z: 504 (M$^+$+1)
(13) Sodium {3-{[2-(4,5-diphenyloxazol-2-yl)-2-cyclohexen-1-yl]hydroxymethyl}phenoxy}acetate IR (Neat): 3500–3300, 1650 cm$^{-1}$NMR (DMSO-d$_6$, δ): 1.2–2.0(5H, m), 2.0–2.2(2H, m), 4.06(2H, s), 4.97(1H, m), 6.5–7.0(4H, m), 7.11(1H, t, J=8 Hz), 7.0–7.8(10H, m) MS m/z: 504 (M$^+$+1)
(14) Sodium {3-{[2-(4,5-diphenyloxazol-2-yl)-1-cyclohexen-1-yl]hydroxymethyl}phenoxy}acetate IR (Neat): 3500–3300, 1650 cm$^{-1}$ NMR (DMSO-d$_6$, δ): 1.2–2.0(4H, m), 4.03(2H, s), 6.5–6.7(2H, m), 6.8–7.0(2H, m), 7.10(11H, t, J=8 Hz), 7.0–7.8(10H, m) MS m/z: 504 (M$^+$+1)

What is claimed is:
1. A compound of the formula:

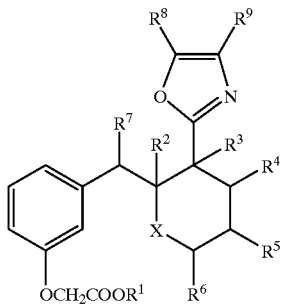

(I)

wherein $R^1$ is a hydrogen atom or a carboxy protective group, $R^2$, $R^5$, $R^6$ and $R^7$ are each a hydrogen atom or a hydroxy group.

$R^3$ and $R^4$ are each a hydrogen atom, or are combined together to form an epoxy group or a single bond, $R^8$ and $R^9$ are each a substituted or unsubstituted aryl group, and X is a single bond or a methylene group, in addition to the above definitions.

$R^2$ and $R^3$ may be combined together to form a single bond; provided that when $R^2$, $R^5$, $R^6$ and $R^7$ are each a hydrogen atom, then $R^3$ and $R^4$ are combined together to form an epoxy group;

when $R^3$ and $R^4$ are combined together to form a single bond, then at least one of $R^2$, $R^5$, $R^6$ and $R^7$ is a hydroxy group and the others are hydrogen; and when $R^3$ and $R^4$ are each a hydrogen atom, then at least one of $R^2$, $R^5$, $R^6$ and $R^7$ is a hydroxy group and the others are hydrogen, and X is a methylene group, or its salt.

2. A compound of claim 1, wherein $R^3$ and $R^4$ are combined together to form a single bond or an epoxy group and $R^8$ and $R^9$ are each a phenyl group.

3. A compound of claim 2, wherein at least one of $R^2$, $R^5$, $R^6$ and $R^7$ is a hydroxy group and the others are hydrogen.

4. A compound of claim 3, wherein one of $R^2$, $R^5$, $R^6$ and $R^7$ is a hydroxy group and the others are hydrogen atoms.

5. A compound of claim 1, wherein $R^1$ is a hydrogen atom or a carboxy protective group, any one of $R^2$, $R^5$, $R^6$ and $R^7$ is a hydroxy group and the others are hydrogen atoms, $R^3$ and $R^4$ are each a hydrogen atom, $R^8$ and $R^9$ are each a phenyl group, and X is a methylene group, or its salt.

6. A compound of claim 1, wherein $R^1$ is a hydrogen atom or a carboxy protective group, any one of $R^2$, $R^5$, $R^6$ and $R^7$ is a hydroxy group and the others are hydrogen atoms, $R^3$ and $R^4$ are combined together to form an epoxy group or a single bond, $R^8$ and $R^9$ are each a phenyl group, and X is a single bond or a methylene group, or its salt.

7. A compound of claim 1, wherein $R^1$ is a hydrogen atom or a carboxy protective group, $R^2$, $R^5$, $R^6$ and $R^7$ are each a hydrogen atom, $R^3$ and $R^4$ are combined together to form an epoxy group, $R^8$ and $R^9$ are each a phenyl group, and X is a single bond or a methylene group, or its salt.

8. A compound of claim 1, which is selected from the group consisting of sodium {3-{[2-(4,5-diphenyloxazol-2-yl)-1-hydroxy-2-cyclohexen-1-yl]methyl}phenoxy}acetate, sodium {3-{[(1S)-2-(4,5-diphenyloxazol-2-yl)-4-hydroxy-2-cyclohexen-1-yl]methyl}phenoxy}acetate, sodium {3-{[(1S)-2-(4,5-diphenyloxazol-2-yl)-2,3-epoxy-1-cyclohexyl]methyl}phenoxy}acetate, sodium (R)-{3-{[2-(4,5-diphenyloxazol-2-yl)-1-hydroxy-2-cyclohexen-1-yl]methyl}-phenoxy}acetate, sodium {3-{[(1R,2S)-2-(4,5-diphenyloxazol-2-yl)-1-hydroxy-1-cyclohexyl]methyl}phenoxy}acetate, sodium (S)-{3-{[2-(4,5-diphenyloxazol-2-yl)-1-hydroxy-2-cyclohexen-1-yl]methyl}phenoxy}acetate, sodium (S)-{3-{[2-(4,5-diphenyloxazol-2-yl)-1-hydroxy-2-cyclopenten-1-yl]methyl}phenoxy}acetate, sodium (R)-{3-{[2-(4,5-diphenyloxazol-2-yl)-1-hydroxy-2-cyclopenten-1-yl]methyl}phenoxy}acetate, sodium {3-{[(1S,2R,3S)-2-(4,5-diphenyloxazol-2-yl)-2,3-epoxy-1-cyclohexyl]methyl}phenoxy}acetate, sodium {3-{[(1S,2S,3R)-2-(4,5-diphenyloxazol-2-yl)-2,3-epoxy-1-cyclohexyl]methyl}phenoxy}acetate, and sodium {3-{[-(1S)-2-(4,5-diphenyloxazol-2-yl)-2,3-epoxy-1-cyclopentyl]methyl}phenoxy}acetate.

9. A process for preparing a compound of the formula:

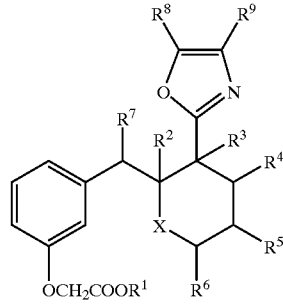

(I)

wherein $R^1$ is a hydrogen atom or a carboxy protective group, $R^2$, $R^5$, $R^6$ and $R^7$ are each a hydrogen atom or a hydroxy group, $R^3$ and $R^4$ are each a hydrogen atom, or are combined together to form an epoxy group or a single bond, $R^8$ and $R^9$ are each a substituted or unsubstituted aryl group, and X is a single bond or a methylene group, in addition to the above definitions, $R^2$ and $R^3$ may be combined together to form a single bond; provided that when $R^2$, $R^5$, $R^6$ and $R^7$ are each a hydrogen atom, then $R^3$ and $R^4$ are combined together to form an epoxy group;

when $R^3$ and $R^4$ are combined together to form a single bond, then at least one of $R^2$, $R^5$, $R^6$ and $R^7$ is a hydroxy group and the others are hydrogen; or when $R^3$ and $R^4$ are each a hydrogen atom, then at least one of $R^2$, $R^5$, $R^6$ and $R^7$ is a hydroxy group and the others are hydrogen, and X is a methylene group,
or its salt,
which comprises
(1) reacting a compound of the formula:

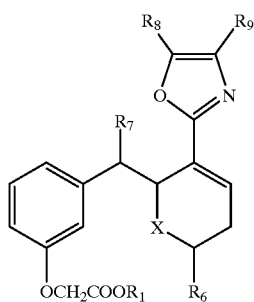

(II-1)

or its salt, in an oxidation reaction] to give a compound of the formula:

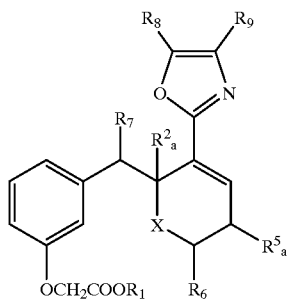

(I-1)

or its salt,
wherein $R^1$, $R^6$, $R^7$, $R^8$, $R^9$ and X are as defined above, and
any one of $R^2_a$ and $R^5_a$ is a hydroxy group and the other is a hydrogen atom or a hydroxy group, (2) reacting a compound of the formula:

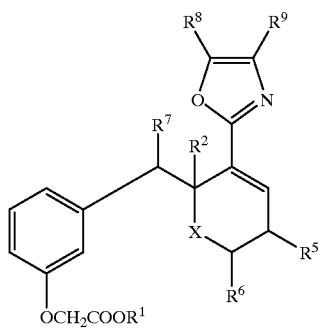

(I-2)

or its salt, in an epixdation reaction] to give a compound of the formula:

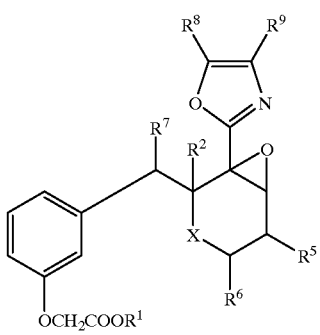

(I-3)

or its salt,
wherein $R^1$, $R^2$, $R^5$, $R^6$, $R^7$, $R^8$, $R^9$, and X are as defined above, (3) cyclizing a compound of the formula:

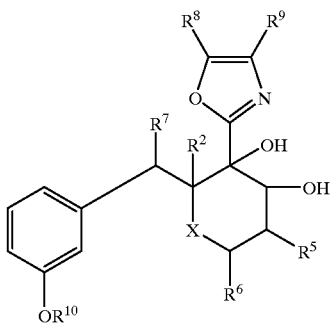

(II-2)

or its salt, to remove $R^{10}$ and then reacting with $Y^1$—$CH_2COOR^1$ to give a compound of the formula:

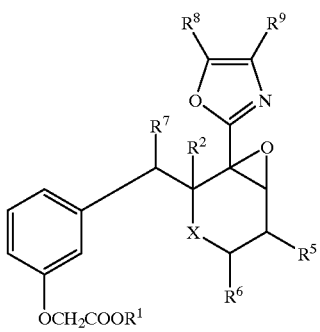

(I-3)

or its salt,
wherein $R^1$, $R^2$, $R^5$, $R^6$, $R^7$, $R^8$, $R^9$ and X are as defined above,
$R^{10}$ is a hydroxy protective group, and
$Y^1$ is a leaving group, (4) removing $R^{10}$ from a compound of the formula:

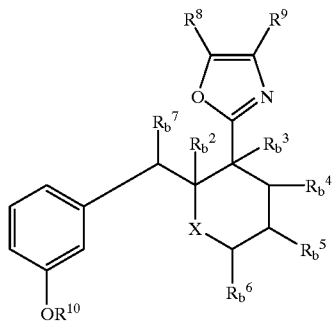
(II-3)

or its salt, and reacting with $Y^1$—$CH_2COOR^1$, followed by removal of hydroxy protective groups for $R^2_b$ to $R^7_b$ if any, to give a compound of the formula:

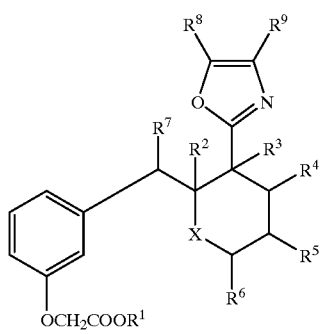
(I-4)

or its salt, wherein $R^1$, $R^2$, $R^3$, $R^4$, $R^5$, $R^6$, $R^7$, $R^8$, $R^9$ and X are as defined above, $Y^1$ is a leaving group, $R^2_b$, $R^5_b$, $R^6_b$ and $R^7_b$ are each a hydrogen atom, a hydroxy group or a protected hydroxy group, and $R^3_b$ and $R^4_b$ are each a hydrogen atom or combined together to form a single bond, in addition to the above definitions, $R^2_b$ and $R^3_b$ may be combined together to form a single bond, or (5) hydrolyzing a compound of the formula:

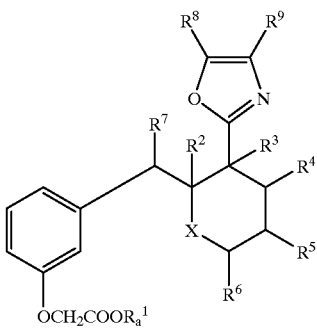
(I-5)

or its salt, to give a compound of the formula:

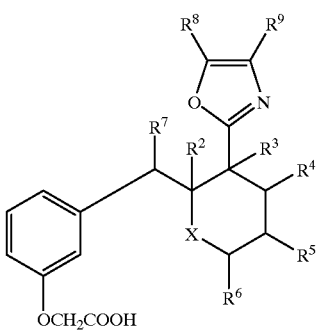
(I-6)

or its salt, wherein $R^2$, $R^3$, $R^4$, $R^5$, $R^6$, $R^7$, $R^8$, $R^9$ and X are as defined above, and $R^1_a$ is a carboxy protective group.

10. A pharmaceutical composition which comprises, as an active ingredient, a compound of claim 1 or a pharmaceutically acceptable salt thereof in admixture with a pharmaceutically acceptable carrier.

11. A method for treating arterial obstruction, restenosis after percutaneous iransluminal coronary angioplasty, arteriosclerosis, cerebrovascular disease or ischemic heart disease which comprises administering an effective amount of a compound of claim 1 or a pharmaceutically acceptable salt thereof to a human being or animal.

12. A process for preparing a pharmaceutical composition which comprises admixing a compound of claim 1 or a pharmaceutically acceptable salt thereof with a pharmaceutically acceptable carrier.

13. A method of inducing prostaglandin $I_2$ agonist activity comprising, administering to a subject in need thereof an effective amount of a compound of claim 1 or a pharmaceutically acceptable salt thereof.

* * * * *